US009719948B2

(12) United States Patent
Charette et al.

(10) Patent No.: US 9,719,948 B2
(45) Date of Patent: Aug. 1, 2017

(54) AIR SLIDE ANALYZER SYSTEM AND METHOD

(71) Applicant: XRSciences LLC, Carlsbad, CA (US)

(72) Inventors: Colin Charette, Encinitas, CA (US); Tom Atwell, Carlsbad, CA (US); Jacob Lopp, Fort Worth, TX (US); Chaur-Ming Shyu, San Diego, CA (US)

(73) Assignee: XRSCIENCES, LLC, Carlsbad, CA (US)

( * ) Notice: Subject to any disclaimer, the term of this patent is extended or adjusted under 35 U.S.C. 154(b) by 0 days.

(21) Appl. No.: 15/287,881

(22) Filed: Oct. 7, 2016

(65) Prior Publication Data

US 2017/0023500 A1    Jan. 26, 2017

Related U.S. Application Data

(63) Continuation of application No. 14/700,417, filed on Apr. 30, 2015, now Pat. No. 9,500,604.

(60) Provisional application No. 61/996,152, filed on Apr. 30, 2014.

(51) Int. Cl.
*G01N 23/222*    (2006.01)
*G01T 3/02*    (2006.01)
*G01N 23/083*    (2006.01)

(52) U.S. Cl.
CPC ......... *G01N 23/222* (2013.01); *G01N 23/083* (2013.01); *G01T 3/02* (2013.01); *G01N 2223/071* (2013.01); *G01N 2223/076* (2013.01); *G01N 2223/0745* (2013.01); *G01N 2223/635* (2013.01)

(58) Field of Classification Search
CPC ....... G01T 3/02; G01N 23/083; G01N 23/222
See application file for complete search history.

(56) References Cited

U.S. PATENT DOCUMENTS 5,691,921 A    11/1997   Berlin
2003/0152186 A1    8/2003   Jurczyk
2007/0295911 A1    12/2007   Sved

*Primary Examiner* — David Porta
*Assistant Examiner* — Faye Boosalis
(74) *Attorney, Agent, or Firm* — Manuel de la Cerra

(57) ABSTRACT

Systems and Methods for an air slide analyzer for measuring the elemental content of aerated material traveling by air slide. The air slide analyzer has an analyzer having an entrance opening and an exit opening, and an interior tunnel adapted for aerated material conveyed by an air slide; a radiation detector proximal to the analyzer; a neutron source emitting neutrons into material within the analyzer; and a processor to analyze detected information from the radiation detector, wherein emissions from the material being irradiated with neutrons are detected by the radiation detector and analyzed by the processor to provide elemental information of the material in the analyzer.

20 Claims, 15 Drawing Sheets

AIR SLIDE ANALYZER SYSTEM AND METHOD

1.0 RELATED APPLICATION

This application claims priority to U.S. application Ser. No. 14/700,416, filed on Apr. 30, 2015, entitled "Air Slide Analyzer System and Method," which claims priority to U.S. Provisional Patent Application No. 61/996,152, filed Apr. 30, 2014 titled "Air Slide Analyzer," the contents of both are hereby incorporated by reference in its entirety.

FEDERALLY-SPONSORED RESEARCH OR DEVELOPMENT

This invention was made with Government support under grant No. 1152704 awarded by the National Science Foundation. The Government has certain rights to this invention.

2.0 FIELD

The present invention generally pertains to systems and methods for analyzing bulk materials. More particularly, it relates to an in-line analyzer for bulk materials with a specially designed air slide.

3.0 BACKGROUND

In manufacturing plants, bulk material is transported using various techniques. For instance, the material may be transported used using front end loaders, physical labor, conveyors, lifts, bucket elevators or pipes. One transportation approach that is in widespread use is to transport the material on a slightly inclined duct of fluidized air, referred to herein as an air slide.

An air slide is a system that uses the force of gravity to move the material. Air slides (also known as aeration conveyors) are used to convey powders using gravity by passing low-pressure air through a porous membrane media into the bed of the material being handled, resulting in the material becoming fluidized. Material movement is achieved by sloping the air slide to match the fluidized angle of repose of the material. At the correct slope, fluidized material will "flow" with the consistency of a liquid.

Air slides are typically used to transport material that generally has a granular consistency of flour, or powder. Examples of materials that are transported by air slide include raw meal and finished cement in cement plant operations. In many industries, it is beneficial to have measurements of the physical properties and composition of the material being transported. This information is used in various ways, for instance in verifying that the material is the correct blend or mixture of material, that the material has the correct material properties, or in using material properties to optimize the manufacturing process. Different measurements can be taken, including the elemental composition of the material, the molecular composition of the material, the granular size of the material, the reflectance of the material, the density of the material, and so forth. The exact measurements depend on the requirements for the application.

Various systems in the prior art have been developed to address quasi-real time assessment of moving material, primarily for non-air slide systems. For example, an in-line analyzer that is in wide spread use is a conveyor-belt analyzer using a technology called Prompt Gamma Neutron Activation Analysis (PGNAA). PGNAA uses thermal neutrons to measure the elemental composition of material on a conveyor belt. However, these systems work on conveyor belts and do not work on air slides. This is because both the low density of the material and the air slide geometrical differences render current technology unfavorable for PGNAA. An approach used on air slides is Near Infra-Red (NIR), but this is a surface measurement, and this measurement is not accurate because of inaccuracies due to changing characteristics of the material and layering in the material. To date, there is no highly accurate system for measuring fluidized material in an air slide.

Therefore, there has been a long-standing need in the industry for accurate, higher-performing air slide analyzers. Various details of such analyzers are elucidated in the following description.

4.0 SUMMARY

The following presents a simplified summary in order to provide a basic understanding of some aspects of the claimed subject matter. This summary is not an extensive overview, and is not intended to identify key/critical elements or to delineate the scope of the claimed subject matter. Its purpose is to present some concepts in a simplified form as a prelude to the more detailed description that is presented later.

An air slide analyzer for measuring the elemental content of aerated material traveling by air slide is disclosed. The air slide analyzer includes an analyzer having an entrance opening, an exit opening, and an interior tunnel adapted for aerated material conveyed by an air slide. The analyzer also includes an air slide that is adjacent to the tunnel and a radiation detector proximal to the analyzer. The analyzer has a source of neutrons, which emits neutrons into material within the analyzer, and a processor to analyze detected information from the radiation detector, wherein emissions from the material being irradiated with neutrons are detected by the radiation detector and analyzed by the processor to provide elemental information on the material. The analyzer also includes a mechanism for increasing a mass per length of material of the material above a mass level per length flowing in a standard air slide section without an analyzer.

In another aspect of the disclosed embodiments, the air slide analyzer described above is provided, wherein the analysis is at least one of prompt gamma neutron activation analysis (PGNAA), Thermal Neutron Analysis (TNA), Pulsed Fast Neutron Analysis (PFNA), Pulsed Thermal Neutron Analysis (PTNA), Pulsed Fast Thermal Neutron Analysis (PFTNA) and Fast Neutron Analysis (FNA). The air slide analyzer may further comprise a complimentary measurement system using at least one of Laser induced breakdown spectroscopy (LIBS), Near infrared imaging (NIR), spectral imaging, X-ray diffraction, X-ray fluorescence, and Nuclear Magnetic Resonance, wherein the radiation source is at least one of a radioisotope neutron source and a controllable neutron generator. The air slide analyzer may further comprise an air slide in the tunnel, wherein a portion of the air slide within the air slide analyzer may be comprised of a material that absorbs fewer neutrons than steel or aluminum. The air slide analyzer may have a mechanism wherein at least one movable gate is disposed within the air slide, and/or a mixer in the tunnel, the mixer mixing material in the tunnel for homogenization, either before or within in a material accumulation area of the tunnel. The air slide analyzer may further comprise at least one of a heater and cooler to heat or cool the detector or control the detector temperature, and/or an active cooling channel between the air slide and the detector, and/or a neutron moderator to optimize signal from the air slide analyzer. The air slide analyzer may further comprise at least one of a gamma ray absorber and/or a neutron absorber disposed about the analyzer, to minimize direct and/or indirect background radiation that would contribute to an external biological radiation dose emanating from the air slide analyzer, and/or shielding located on at least one of a front, side, top, bottom and back area arranged to reduce external radiation for biological shielding, wherein the analyzer may be comprised of a plurality of substantially uniformly shaped individual shielding pieces, enabling the analyzer to be constructed or dismantled in a piece-wise manner. The analyzer may be constructed to accommodate different shielding requirements or different air slide sizes, and may further comprise an opening within the air slide for physically sampling material directly from the air slide and and/or placing a calibration standard in the air slide, wherein the air slide may be comprised of multiple sections, and the individual air slide section(s) may be replaced for maintenance or for calibration purposes by a standard section(s) of an air slide. Furthermore, the accumulation area of the air slide in the body may be designed with a shape and size that improves a signal accuracy of the air slide analyzer. The portion of the air slide may be dimensioned from 6" wide to 36" wide, as a non-limiting example, and the material in the air slide could be at least one of: raw meal, finished cement, a blend of finished cement and aggregates, ready-mix concrete, fly ash, gypsum, limestone, clinker, off-spec clinker, bottom ash, slag, beneficiated fly ash, lime, silica fume, ground granulated blast furnace slag, shale, sand, sandstone, iron more, bauxite, volcanic ore, and ash. The air slide analyzer may further comprise silos containing at least one of these materials, wherein the processor may send information for adjusting an amount of material supplied from the silos based on the at least one molecular and elemental composition of the material in the air slide, and/or measurement information from one or more cross belt PGNAA systems, wherein the air slide analyzer may be a part of a processing plant.

Additional aspects, alternatives and variations as would be apparent to persons of skill in the art are also disclosed herein and are specifically contemplated to be included as part of the invention. The invention is set forth only in the claims as allowed by the patent office in this or related applications, and the following summary descriptions of certain examples do not in any way limit, define or otherwise establish the scope of legal protection.

5.0 BRIEF DESCRIPTION OF THE DRAWINGS

6.0 DETAILED DESCRIPTION 6.1 Introduction

A method of analysis for in-line conveyor belt analyzers that is in wide use is Prompt Gamma Neutron Activation Analysis (PGNAA). PGNAA uses thermal neutrons to measure the elemental composition of material on a conveyor belt. This technique is especially useful for bulk material analysis, as the technique is deeply penetrating and can measure most if not all of the material on a conveyor belt. Thus, unlike other techniques such as X-ray diffraction and X-ray fluorescence, which use surface measurements, PGNAA analyzers are capable of measuring large quantities and depths of material. Another significant benefit of PGNAA is that the measurement is non-contact and PGNAA equipment has few, if any, moving parts.

As a result of the capability and benefits of PGNAA, PGNAA equipment is in widespread use throughout the coal, cement and minerals markets. In the cement market, PGNAA is typically used for the analysis and blending of raw materials. The raw material from the cement plant is extracted from the quarry, mine, silo, or pile, typically crushed, and then analyzed using the PGNAA equipment.

Figure 1:
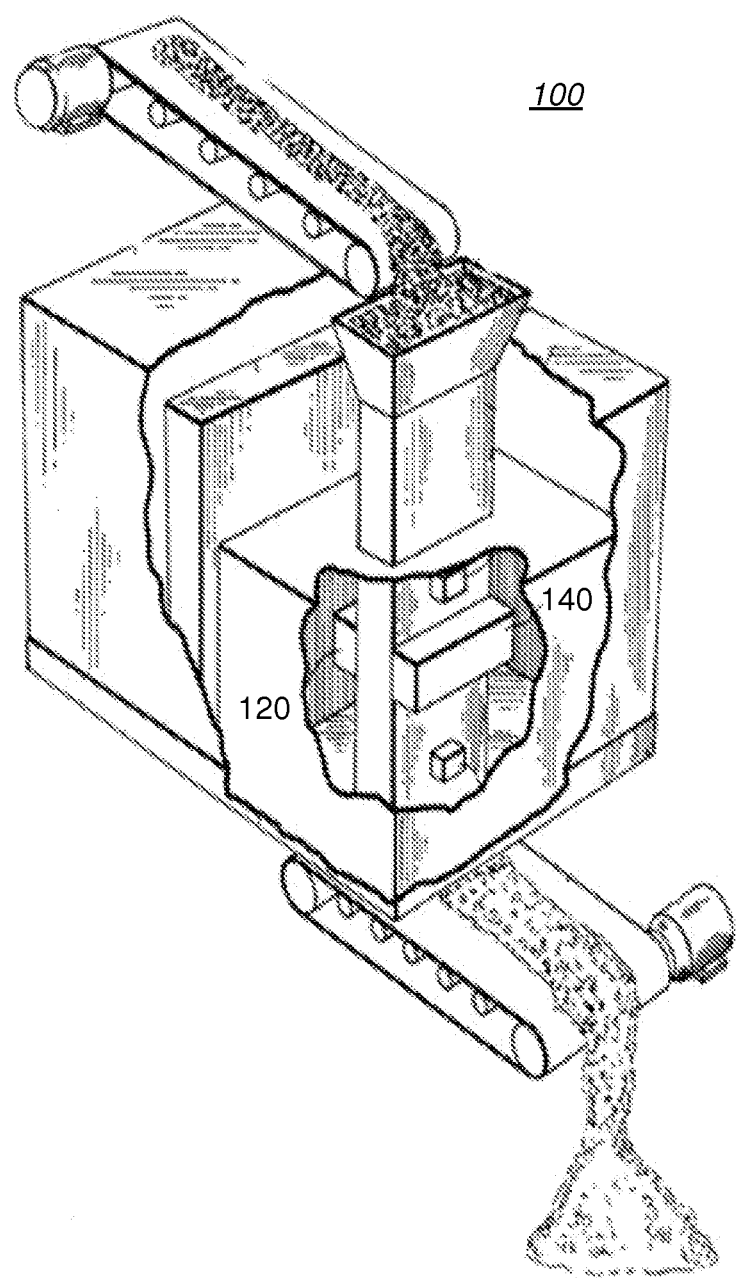
FIG. 1 is a perspective view of a related art chute analyzer.
Figure 2A:
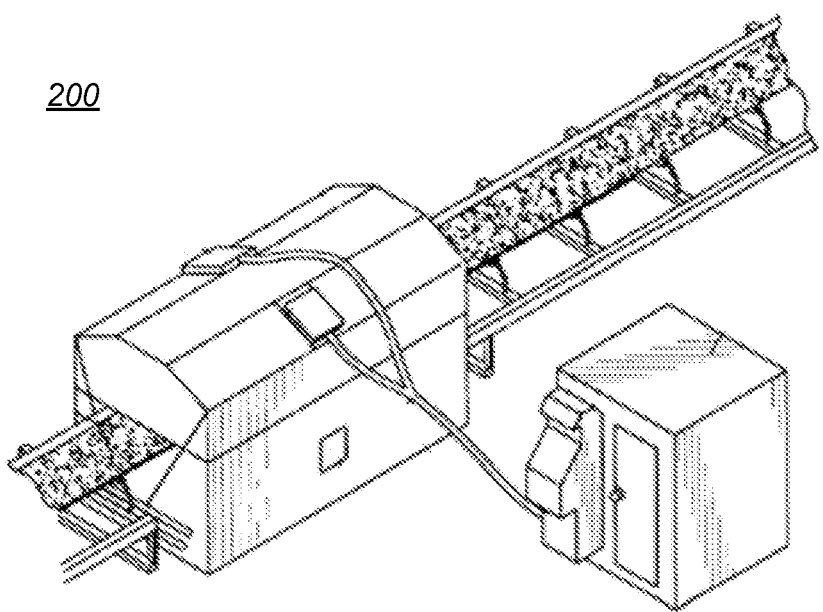
FIG. 2A is a perspective view of a related art conveyor belt analyzer.
Figure 2B:
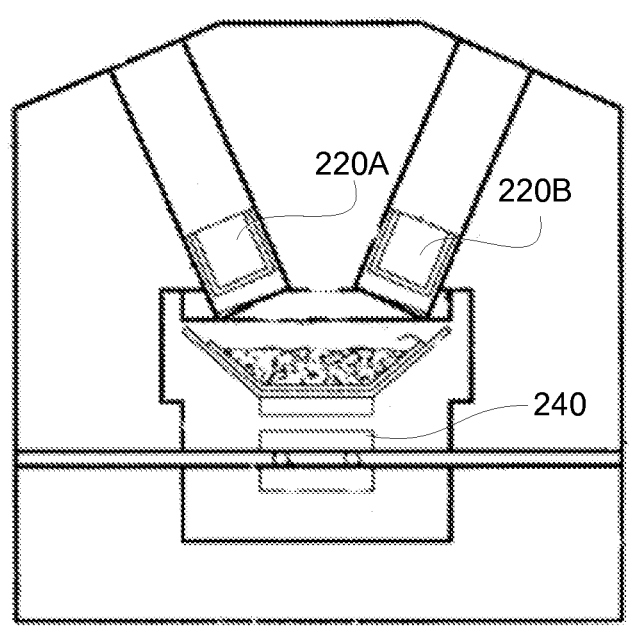
FIG. 2B is a cross-sectional view of the related art conveyor belt analyzer of FIG. 2A.

Early PGNAA equipment used a drop chute-type of analyzer as shown in the related art illustration 100 of FIG. 1, having detector 120 and source 140 on opposite sides. An example of this system is described in U.S. Pat. No. 4,582,992, titled "Self-Contained, On-line, Real-Time Bulk Material Analyzer," by Atwell et al. These types of analyzers were useful, but expensive, and difficult to install at a plant. This problem was solved with the development of on-line conveyor-belt type PGNAA analyzers. One related art analyzer system 200 is shown in perspective and cross-sectional views in FIGS. 2A and 2B, respectively. The mechanics of such a system are described in U.S. Pat. No. 5,396,071, titled "Modularized Assembly for Bulk Material Analyzer," by Atwell et al. These cross-belt systems were significantly easier to install and fit very well into the factory operations; however, they required an arrangement of detectors 220A, 220B above the source 240. Since the development of the first PGNAA on-belt analyzers, the designs have evolved to improve ease of installation and ease of manufacture. Modern PGNAA devices typically mount to the rails of a conveyor belt or straddle the rails mounting to pads on both sides. The devices do not require cutting the conveyor belt, and can be installed and calibrated in a few days.

Figure 3:
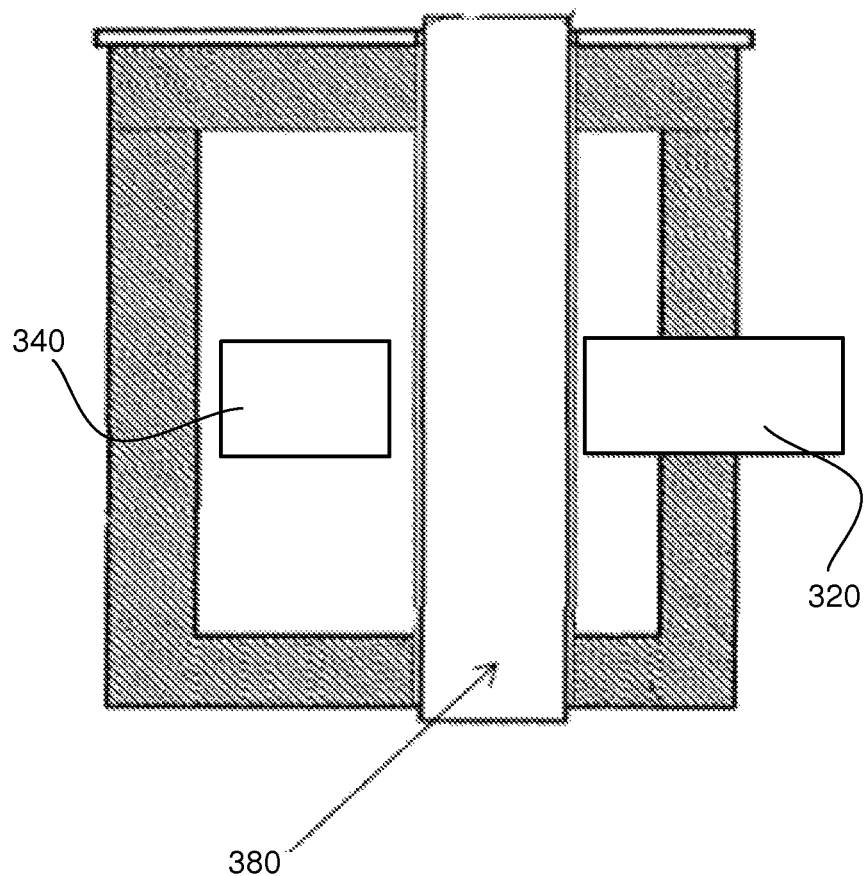
FIG. 3 is a diagram of a related art analyzer where the material flows thorough the analyzer.

Other PGNAA analyzers used for on-line and off line analysis have been developed. For example, the analysis of the material can be done through a pipe 380 with externally arranged source 340 and detector 320, as shown in the related art illustration 300 of FIG. 3 and described in U.S. Pat. No. 7,778,783, titled "Method and Apparatus for Analysis of Elements in Bulk Substance," by Lingren et al. This patent includes a description of the common types of PGNAA systems, such as static analyzers, slurry analyzers, mechanical sampler analyzers, conveyor analyzer, and drill tailings analyzers.

PGNAA analyzers in service today often have performance issues. For example, in cross-belt PGNAA analyzers, layering of material may occur, which will impact the accuracy of the analysis. Techniques have been developed to compensate for this. For example, U.S. Pat. No. 6,657,189, titled "Maintaining Measurement accuracy in Prompt Gamma Neutron Activation Analyzers with Variable Material Flow Rates or Material Bed Depth," by Atwell et al., developed an error correction technique to compensate for layering.

Another issue that may arise in PGNAA analysis is due to the varying moisture content of materials. Different amounts of moisture in the material may change the thermal neutron density as a function of the depth of the material, and as a result may impact the prompt gamma ray production and emitted spectrum as a function of material depth. PGNAA analyzers often have moisture meters to measure the moisture content, and this information may be used to allow for compensation for varying degrees of moisture in a material. However, having to use compensation corrections typically diminishes the accuracy of PGNAA devices.

Bulk material is transported with various approaches, but a great deal of material is transported through conveyor belts. As a result, the vast majority of PGNAA analyzers to date are of the belt-conveyor type and provide an elemental analysis of material on a conveyor belt.

In some instances, 'additive' materials may be added to the manufacturing process downstream of the conveyor belt analyzer. For example, in cement plants, fly ash, slags, baghouse dust or other materials may be added to the manufacturing process after the cross belt analyzer point of measurement, which will result in greater uncertainly to the composition of the kiln feed.

Figure 4:
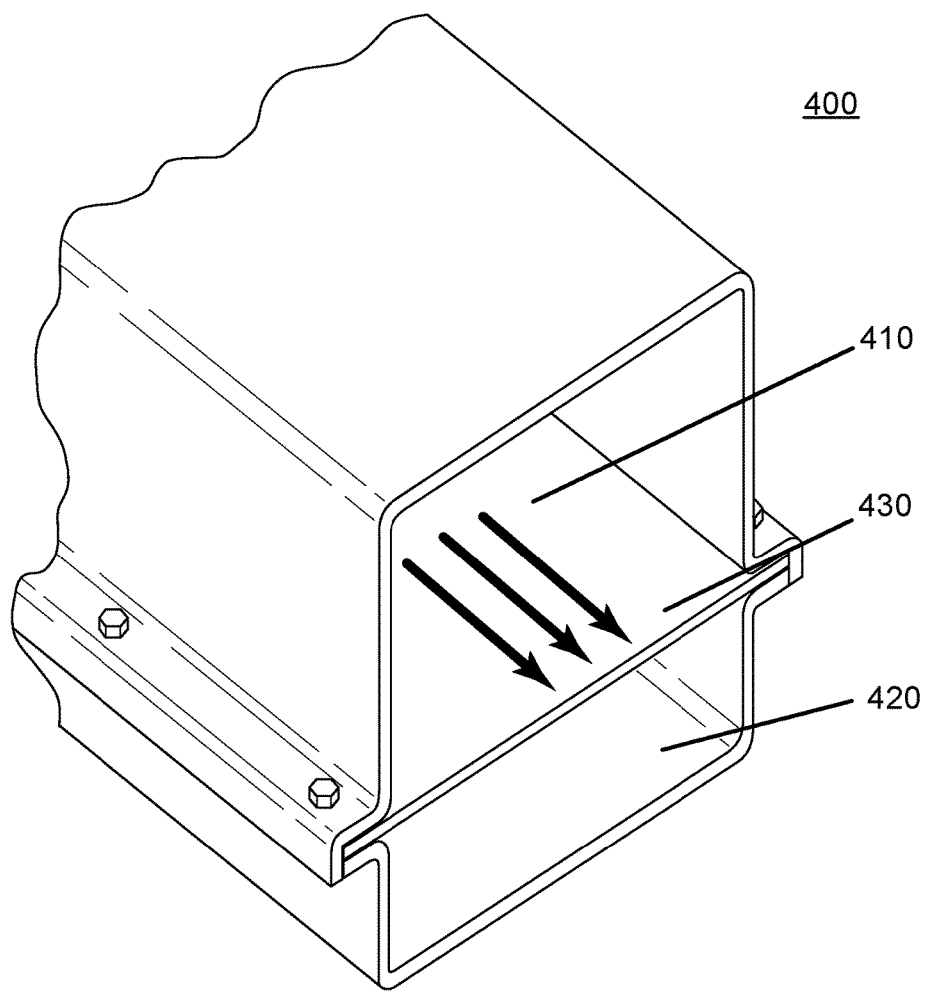
FIG. 4 is a perspective view of a related art air slide.

In the cement industry and other industries, material is transferred by conveyor belt as rock product and ore from the quarry to the point in the process where it is milled. To prepare the raw material for use in the cement kiln, the raw material is milled so that it has a powder-like consistency similar to that of flour. To transport this material, bucket elevators and air slides are often used, not a conveyor belt. An air slide uses the combination of air and gravity to transport the material. A related art air slide using air and gravity is shown in FIG. 4. Air is blown in from an air chamber below the bulk material. The air goes through a porous membrane fabric, and into the tunnel containing the material. The air fluidizes the material. By angling the air-slide downward a few degrees, the fluidized material travels along the air slide with little friction or compressed energy required. However, the application of PGNAA measurement systems to air slide systems has never been done because of the low density of the material, which increases difficulty in making accurate and timely measurements.

PGNAA technology, such as that of on-belt analyzers, usually requires the exposure of many atoms to do an accurate analysis or significant hydrogen content to enhance the reaction rates in low density materials. On conveyor belt or slurry type analyzers, the material may be mineral ore or rock/sand product aggregate with bulk density ranging 1.5-1.7 g/cc, crushed coal of density 0.8 to 0.9 g/cc but with hydrogen percentage 3.5 to 6%, or a mineral-water slurry with density 1.1 to 1.35% and hydrogen content of 8-10%. Hydrogen in the sample may moderate the neutrons' energy down to a level where the atoms in the material have a significantly greater probability of absorbing neutrons and therein producing gamma ray emission.

Assuming the detection system is not limited by signal rate, PGNAA measurement precision is primarily a function of the number of neutrons induced and captured in the material being measured (proportional to the total mass of material in the measurement zone and the percent hydrogen in the sample, which increases the material neutron capture probability), or the product of the combined geometric solid angle of the detection apparatus, the intrinsic gamma ray efficiency of the detectors used, and a function of the energy resolution (spectral clarity or acuteness) of detector and signal processing electronics. In an air slide, the material is in dry powder form: bulk density may be low (0.75 to 0.85 g/cc); moisture and hydrogen may be essentially zero; and the material levels in an air slide are generally only 25-50% of the air slide's volume and the air plenum at the bottom is void of material, which results in significantly fewer atoms available on a per volume basis for analysis.

These considerations present problems with the accuracy of PGNAA techniques when applied to air slides. It would be beneficial, therefore, to have a high precision elemental analysis of the material in the air slide. For example, in cement manufacturing, the analysis would then include any material, such as fly ash, added to the air slide after the milling stage. Another location where an air slide analyzer would be valuable is later in the cement manufacturing process, after the clinker is milled to a powder, when additives such as gypsum or limestone are added. An air slide analyzer would provide valuable process feedback to allow the operators to validate and optimize the manufacturing process. Also, since material transported by an air slide has to be sufficiently dry to properly move in an air slide, an air slide analyzer would in part need to address the issue of varying moisture content in the material.

An attempt to address the above concerns can be found in U.S. Pat. No. 7,924,414, titled "Non-hazardous Bulk Material Analyzer System," to M. Mound, which is a method of measuring the composition of the material in an air slide using a light source and a spectrometer. However, the light source and spectrometer only enable surface measurements, which falls far short of analyzing the full composition of the material. Also, biases in the data can result, as the technique is based on the spectral reflectance of the material, and is not a direct measurement of the elemental composition of the material. Yet another issue is that there may be lighter and heavier materials in the material mixture, and so segregation and layering is highly likely, such that a surface measurement will not be representative of the entire material traveling through the analyzer.

6.2 Overview

In view of the above, various embodiments described herein present an in-line analyzer that measures the elemental composition of material transported in air slides. The mechanical arrangement of analyzer components in combination with component additions and modifications to the air slide before, within, and after the analyzing zone is designed to deliver significantly higher performance than conventional PGNAA analyzer designs that mount around conveyor belts or slurry tubes. The configuration of the PGNAA system geometry (analyzer complete with a modified air slide) will optimize the resulting signal from the system. By using a new unique system design, it is possible to greatly increase the sensitivity of the PGNAA device. Accordingly, an accurate, high precision elemental analysis of the material being transported in an air slide can be achieved such that it can be used for monitoring, process control and other uses.

To measure all of the material in the air slide, the technique called prompt gamma neutron activation analysis (PGNAA) is used. In this technique, neutrons enter the material to be analyzed, and from the neutron interaction with the material, gamma rays are emitted by the material. The gamma rays emitted by the material from the neutron stimuli are analyzed to determine the elemental composition of the material. The embodiments described herein are not limited to PGNAA, but can also use fast or thermal neutrons, or a combination of fast and thermal neutrons. Terms commonly used are PGNAA, Thermal Neutron Analysis (TNA), Pulsed Fast Neutron Analysis (PFNA), Fast Neutron Analysis (FNA), are well-known to those with expertise in this art. The approach can be continuous or be in pulsed operations. The source of neutrons can come from an isotopic source, or alternatively from a neutron generator, or a combination of both. In various embodiments, the system includes the air slide transport mechanism, the neutron source, and the radiation detector. The material enters the air slide analyzer, and neutrons diffuse into the material. When the material captures or inelastically scatters the neutrons, gamma rays are emitted within a very small fraction of a second. The emissions (a spectrum of gamma rays) are analyzed to determine the elemental composition.

In various embodiments, the system includes a method of providing more material for the analysis, which can improve the accuracy of the analysis. For example, more material is provided by restricting or configuring a restriction zone for the flow of material such that the material accumulates inside the analyzing zone. At some point downstream, the material may be allowed to return to its normal level and flow characteristics.

Since aerating a material composed of a blend of different density particulates having a different chemistry can result in spatial inhomogeneity within the mix flowing in the air slide, the spatial inhomogeneity can undesirably fluctuate depending on the mass flow rate. And depending upon the arrangement of the exemplary analyzing apparatus (source(s), detector(s)) with respect to the material, the material inhomogeneity can lead to measurement errors. To alleviate this potential problem, various embodiments may include the option of adding a means of mixing the material "in" the analyzer or "before" the material enters the analyzer. To ensure that the analysis is not biased by a portion of material of a given chemistry entering the analyzer, and because of characteristics such as density or lack of fluidization, the system can further include a method of ensuring that the material of any physical nature remains fluidized and moves through the analyzer without holdup.

Since material inside an air slide may be quite hot, as in raw meal, the exemplary embodiments may incorporate a means of ensuring that the temperature of the detectors and the system is consistent and will not damage the system.

Various embodiments can be further designed to optimize the system measurement by using a number of different approaches. For example, the physical locations of the source, detector, material, and the air slide mechanism may be arranged to provide optimal measurement performance while ensuring that the system continues to provide consistent flow characteristics. The normal air slide structural elements (ducts or channels) are typically metallic, typically steel. Strong signals emanate from most metals, reducing the performance of the analyzer. Therefore, in various embodiments the analyzer air slide apparatus is designed and fabricated out of a material that results in better measurement performance in neutron irradiation from the analyzer. The structural material may be a material of a unique signature or doped with a material(s) to provide a unique gamma ray signature that can be differentiated from the signatures of the material being analyzed. This can also be a material that has a low cross section such that it absorbs relatively few neutrons, for example, carbon, or low cross section zirconium, etc.

In other embodiments, the system may be modular, such that it can be easily adjusted and configured for varying sizes of air slides. The modular pieces can be large or small. Small modules are designed to be easily carried by hand, such that the analyzer can be installed in locations where access using a crane or other lifting mechanism is not possible, or at least extremely difficult to access.

The air slide is often in a critical location such that a shut-down of the air slide can potentially stop the manufacturing process. Thus, it is critical that there is a method of ensuring the system does not restrict the flow of material during maintenance, blockages, breakdowns, or system calibrations. In various embodiments, the air slide analyzer may include a drop-in replacement air slide section that is designed to be easily installed in place of the special section that is normally used inside the analyzer, should any flow problem or other failure develop. This provides a method of handling many issues that arise with the air slide, and allows for maintenance on the air slide, repairs on the air slide, calibration of the air slide, while ensuring that plant operations are not adversely impacted. Yet another method is to have a diverting gate that allows the material to flow through the analyzer, and to divert the flow around the analyzer if there are flow issues, maintenance requirements or other situations where it is necessary to divert the flow of material. Another aspect that is important is minimizing radiation from the system. Thus, shielding may be extended to the front or back of the air slide. This may be attached to the analyzer, or made separate. The overall objective is to minimize the dose to the surrounding areas.

Calibration of the system is often critical to the system performance. In various embodiments, the system can be calibrated by either fitting the air slide before or after the analyzer with access ports through which calibration standards can be inserted into the analysis zone, or by doing the calibration off-line by decoupling the special air slide section spanning the analyzer and moving both the air slide section and the analyzer up, down or laterally away from the air slide to allow insertion of the calibration standards through the ends of the analyzer's air slide section. In some embodiments, the analyzer is not equipped with an air slide itself. The air slide analyzer can be attached to the input or discharge end of the air slide to provide the material for analysis. Various embodiments described below include an air slide mechanism, which may ensure that the air flow system has consistent flow characteristics.

In some embodiments, the analyzing means utilizes an X-ray source(s) producing a broad spectrum of x-rays that irradiate the material in the air slide, a detector or detector array on the opposite side of the material where the signal measured is the X-ray source spectrum attenuated by each of the elements composing the material, and a means of quantifying the elemental composition of the material by utilizing the physical property that each element has a unique energy-dependent response function to incident gamma rays that depends on the atom density thickness ($g/cm^2$) of each element in the material composition on the air slide.

It is understood that for PGNAA systems, optimal performance is usually obtained if there is more material inspected rather than less material inspected. When the material is in powder form, it can blow off of a conveyor belt. Therefore, a more efficient and effective method of moving the material when it is in granular or powder form is to move the material by an air slide.

FIG. 4 is an illustration 400 of an air slide. The material (shown as arrows) travels in the material chamber 410 while air is blown from the pressurized air chamber 420 into the material chamber 410. The air from the air chamber 420 travels "upward" through a porous membrane 430 and lifts up the material in the material chamber 410 to aerate the material. The membrane 430 can be of any material, non-limiting examples being a metal screen, air-porous fabric, etc. In some instances the membrane can be vibrated to assist in the lifting up of the material. The air slide is typically on an angle, and as a result, the material travels with the inclination of the material chamber 410.

However, it is understood that the air slide can be horizontal or a combination of angled and horizontal (being sectioned accordingly). Moreover, different portions of the air slide can be at different inclinations (or non-inclinations) within different portions of the analyzer. An alternate way of moving the material may also be by pneumatics, where the material is blown through a pipe or tunnel—not widely used because the inherent efficiency of an air slide requires significantly less power to operate. The material may be in a powder form, a granular form, but can be prepared so that it is suitable for transport in the air slide.

Figure 5:
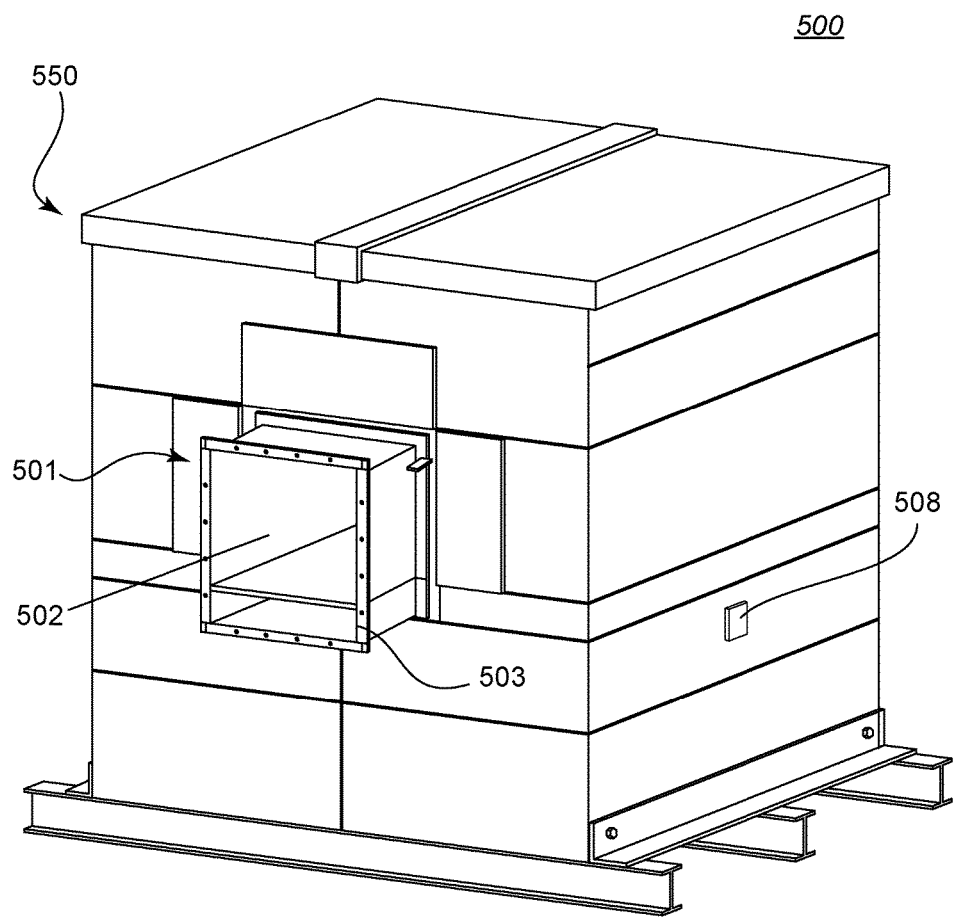
FIG. 5 is a perspective view of an exemplary embodiment of an air slide analyzer.

FIG. 5 is a perspective illustration 500 of an exemplary air slide analyzer embodiment. The air slide 501 travels through the analyzer 550 having entrance and exit portals for the air slide 501, and the material (not shown) is analyzed as it travels through the analyzer 550. The tunnel 502 for the air slide 501 allows the material to pass through the analyzer 550, and the air in the air chamber 503 keeps the material fluidized. Note that it is also possible to design the air slide analyzer without an air chamber 503, where the material slides or travels through the analyzer 550. If it is desired that "fluid" flow is maintained during analysis, an air chamber system may provide less disruptions to the flow of material than other systems. Of course, other configurations for analysis without the use of an air slide may be contemplated without departing from the spirit and scope of this disclosure. Further, while FIG. 5 illustrates an analyzer body about the air slide 501, a configuration can be made where the body is absent, wherein the analyzer 550 is devoid of a solid or body that surrounds the air slide 501.

Since most air slides are made of metal, analyzing the material through a metal air slide can affect the signal from the material in the analyzer 550. Thus, the tunnel 502 and air chamber 503 can be made of a material exhibiting low neutron absorption probability; and with a small percentage of dopant element, which can simultaneously provide a unique signal for overall calibration. Low neutron absorbing materials include carbon fiber, and other low cross section materials, such as composite materials or metals with low neutron cross sections. The tunnel 502, air chamber 503 and surrounding material can be designed to optimize the signal coming from the material traveling through the air slide 501. The analysis can still be done through a steel air slide, but utilizing a more neutron transparent material is understood to minimize the signal alteration or loss from the analyzer 550.

In this illustration 500, a source door 508 is shown on the "right" of the analyzer 550 for placement of the neutron source. However, the source(s) and detector(s) may be positioned around other sides of the air slide 501. It should be appreciated that in some embodiments, the source may be a radioactive isotope or an accelerator or other on-demand neutron/radiation source.

Figure 6:
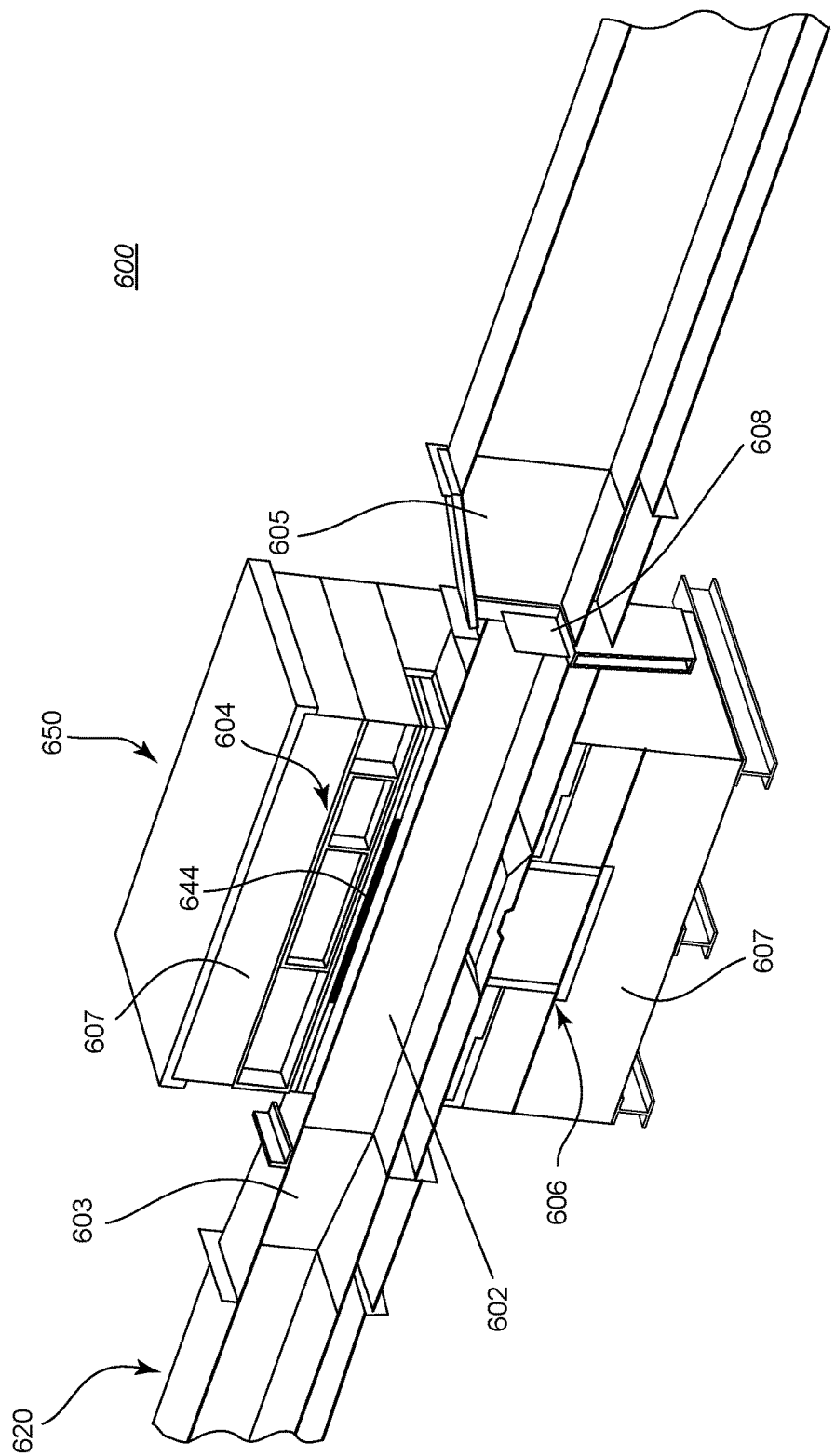
FIG. 6 is a cross-sectional view of one embodiment of an exemplary air slide analyzer.

FIG. 6 is a cross-sectional view 600 of an exemplary air slide analyzer, showing the interior tunnel 602 where the material (not shown) travels through, and buffer regions 603, 605 between the non-analyzer portions of the air slide 620 and the analyzer 650. All neuron activation systems have a source of neutrons 606 and one or more detectors 604. While FIG. 6 illustrates the shown arrangement of sources/detectors 606, 604, other arrangements may be utilized. For example, the sources 606 may be placed along the longitudinal axis of the air slide analyzer 650. The neutron source 606 can be an isotopic source, or alternatively a neutron generator can be used. The detector(s) 604 can be configured longitudinally or perpendicular, or as required to optimize the signal. As with other neutron-based systems, the detector(s) 604 can be heated or cooled.

Alternatively, as the material in the air slide 620 may be hot, the system may also provide cooling (not shown) in case of hot material such as hot meal. This embodiment illustrates the use of top and bottom biological shielding material 607 for radiation safety. The exact material used in the body of the analyzer 650 is also selected taking into account the temperature of the material in the air slide 620, and the ambient temperature around the analyzer 650. For example, for raw meal, the meal can be hot, and thus the detector enclosure may include both heating and cooling mechanism(s) for the detectors 604. In a commercial embodiment, a cooling channel 644 can be implemented between the air slide 620 and the detector apparatus 604, cooled by various passive or active means, non-limiting examples being vents, forced air or compressed air or jets of compressed air cooling by adiabatic expansion, and so forth.

The exemplary air slide analyzer illustrates the use of a gate 608. Material in the air slide 620 acts similarly to a liquid (seeking a near-horizon level), and thus the use of a gate 608 allows material to accumulate inside the analyzer 650. This gate 608 essentially acts as a dam, such that the material accumulates behind the dam. Using the gate 608 to accumulate material will increase the material in the analyzer 650, and can increase the resulting signal of the system. The gate 608 can be lowered or raised to adjust the accumulation to ensure that the flow is suitable for plant operations or the analyzer operations. The gate 608 can be in a section that is separate from the analyzer 650, or it can be incorporated into the analyzer 650. The gate 608 can simply be a piece of metal or suitable material that comes up from the bottom, top or side of the assembly and that inhibits the flow of material. It can also be stationary such that it does not move, similar to a dam with a fixed height. A gate 608 or series of gates 608 could be installed downstream, or upstream, or both to gradually build up the level in the measurement.

Figure 7:
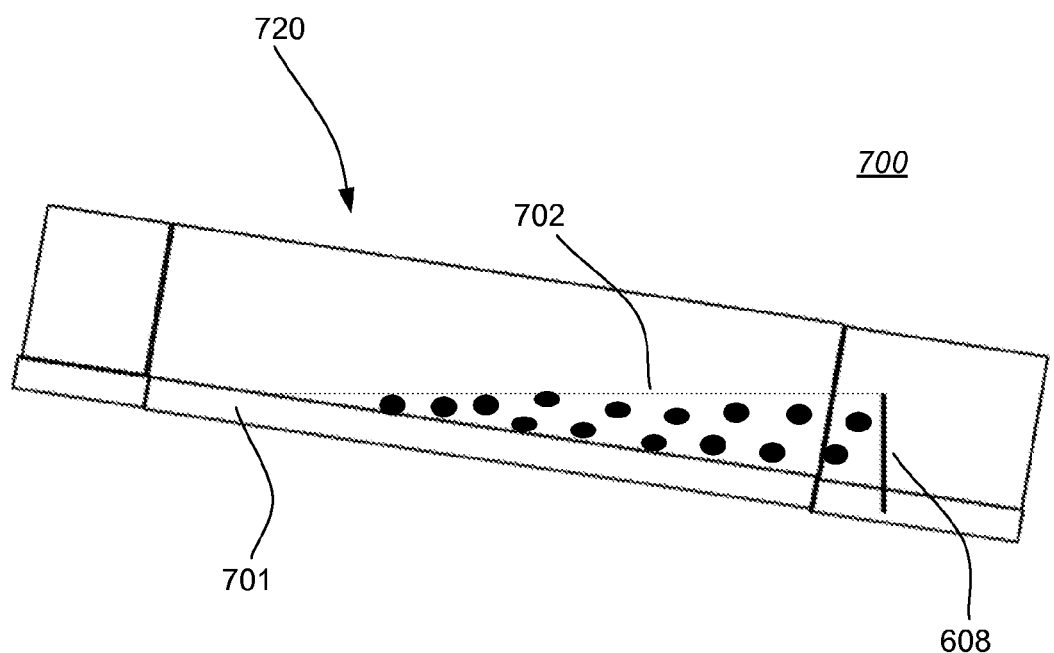
FIG. 7 is a cross-sectional view of an exemplary air slide.

FIG. 7 is a side view illustration 700 of an exemplary air slide 720, with the "below" air chamber 701 and protruding gate 608. The gate 608 acts as a dam, and as a result, the material accumulates to a region defined in this illustration as 702. The analysis zone may be centrally located within the body of the analyzer so as to allow for biological shielding of neutron source radiation on each end. The system may be optimized to analyze material that accumulates in region 702. In various embodiments, the gate height can be adjusted up or down, on side to side to allow for differing volumetric areas or for simply allowing a pre-set volume to build up or pass. Gate(s) 608 are just one method of accumulating material in the analyzer, such as for increasing a mass per length of material of accumulated material above a mass level per length flowing in a standard air slide section without an analyzer. There are numerous other methods or approaches that can be used to accumulate material, non-limiting examples being a trough, pit, sectioned area, narrowed region, etc.

The air slide 720 can be comprised of multiple stages or pieces, allowing an individual or group of pieces to be quickly replaced or exchanged as needed. For example, the gate 608 is shown as being part of the rightmost piece, which may be individually replaced, in the event the gate section requires maintenance.

In another embodiment, the fluidized density of the material in the analyzing zone can be optimally maximized by fabricating the air plenum section with a series of Longitudinal sections, each of which has a separate air supply with adjustable pressure, so as to achieve the optimum fluidization for the level or height of material above. Pressure valves can be controlled by a microcomputer or controller based on a level sensing or mass flow rate apparatus. In some embodiments, a trough may be used in or outside the analyzer. A valve (such as a V-Ball) may also be used in or after the analyzer to increase the amount of material in the analyzer. Another approach is to narrow the width of the material chamber, for example to make it narrower. Yet another approach is to restrict the flow downstream, such that the amount material accumulates in the analyzer. The main objective is to increase the signal by increasing the amount of material in the analysis region.

For ease of operation, the porous material of the air slide 720 "inside" the analyzer (where predominantly the gamma ray spectral measurement signal is generated) can be made of the same material used in the rest of the air slide 720 to ensure the flow of material in the analyzer is consistent with the rest of the air slide 720. In some embodiments, it may be desirable to use a different material, according to design preference. It should be appreciated that while an air chamber 701 is shown in this embodiment, it is not necessarily required, as the material in the analyzer can slide through or be blown through the analyzer without an air chamber 701. However, for ease of operation and flow consistency, the embodiments described herein are shown with an air chamber 701. Accordingly, it is understood that alternative designs may be contemplated absent an air chamber by one of ordinary skill in the art, without departing from the spirit and scope of this disclosure.

Figure 8:
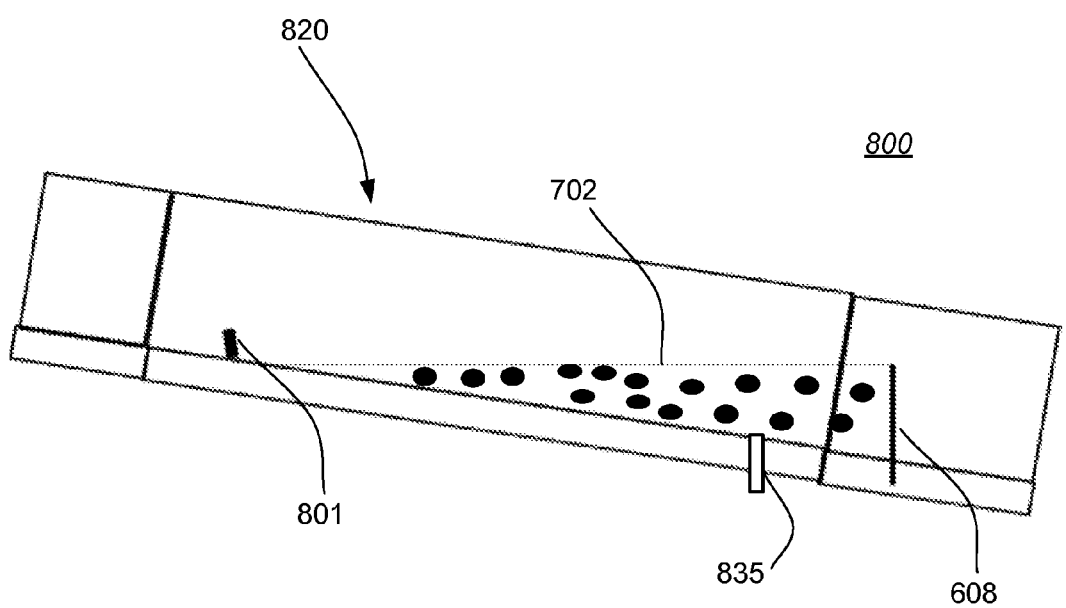
FIG. 8 is a cross-sectional view of another exemplary air slide.

The material sent through the air slide may have a consistent composition, or it may have a composition that is not uniform, and may cause layering. FIG. 8 is an illustration 800 of an embodiment where a disrupter (or homogenizing means) 801, which can be fabricated from metal or other resilient material, possibly bent on an angle is placed in the air slide 820 to cause disruptions in the material or air flow, such that the material is agitated before it accumulates in region 702. There are other methods for mixing of material for homogenization. For example, additional air may be blown or pulsed into region 702. This can be from the bottom, or sides, or top. This same effect can be done by using different porous fabric (possibly having different frictional, or porosity, etc. characteristics) in region 702. Alternately, the system may include some mechanism of mixing the material as it accumulates in the 702 region. This can be accomplished by something as simple as a propeller-type mechanism that can be turned and is located in region 702 or adjacent to disrupter 801. Accordingly, alternative methods for "mixing" can be employed by one of ordinary skill in the art and are understood to be within the purview of this disclosure.

To ensure that the material does not remain static on the gate 608, the gate may include porous material to allow the material to flow through the gate. Alternately, there may be opening or holes in the gate 608 to allow for the material to flow through the gate 608, and not just over the gate 608. An alternate method of ensuring that the material does not accumulate and stays in region 702 is to open and shut the gate 608, or to tilt or turn the gate 608 at periodic intervals, to allow the material to flow through the system. The gate 608 may be of any desired shape or geometry. Various means can be designed to ensure that static material does not remain in the accumulation region 702. Further, various means of raising the material level in the analyzing zone can be under automated control and may utilize level sensing or mass flow feedback or the by analyzer itself through quantitative measurement of the total mass of the constituents analyzed.

In some embodiments, the air slide 820 can have a channel or passage 835 for allowing some material to be directed to a separate analyzing device (not shown) for independent or complementary analysis, for example, elemental or molecular analysis, in order to supplement the neutron analysis being performed. Or, any other section of the air slide 820 that experiences passing material can have the channel or passage 835, for example, the gate 608 or other section may have the channel or passage 835. Moreover, passage 835 may be used to insert an instrument such as for calibration standards or for direct measurement of the passing material.

Figure 9:
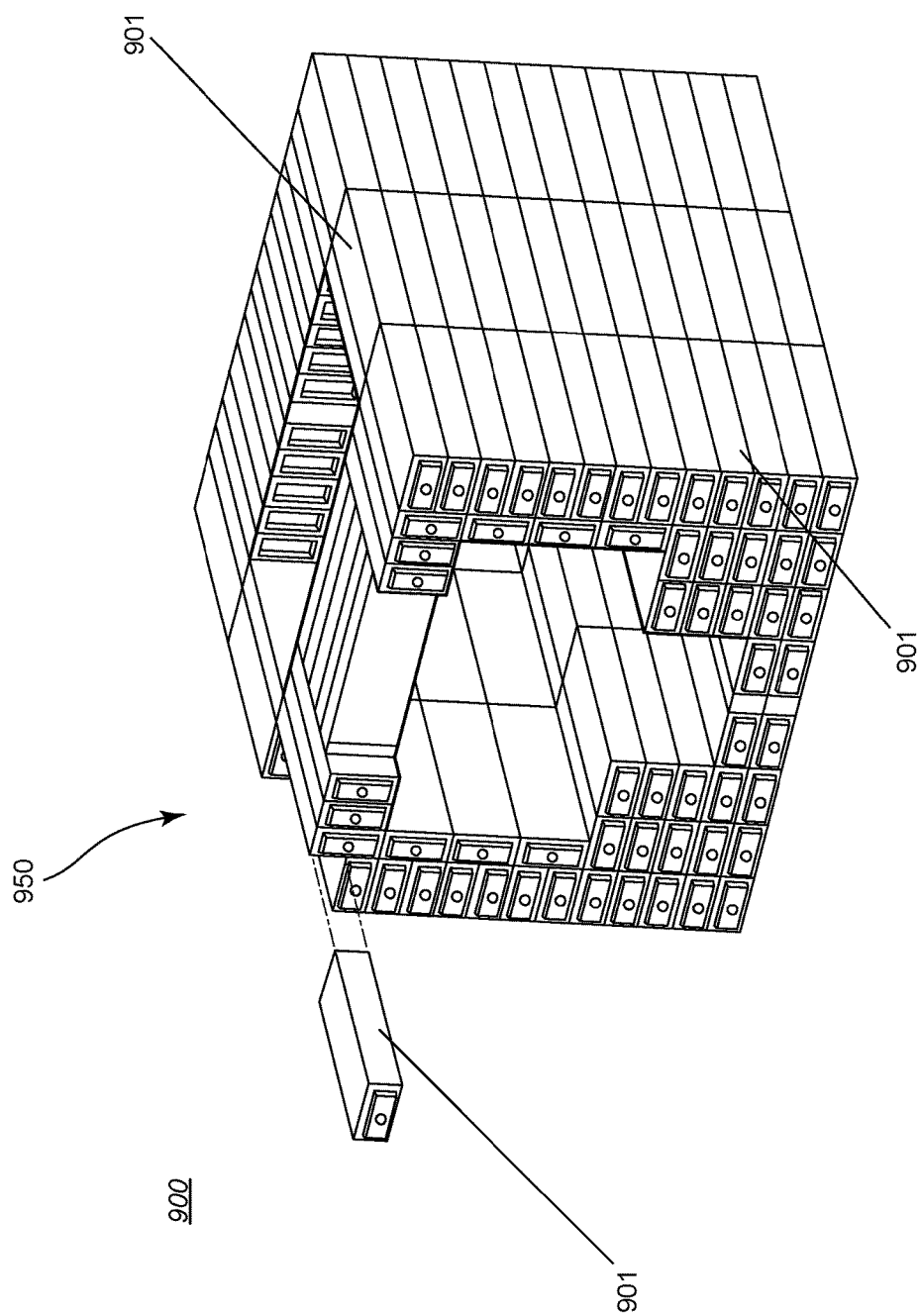
FIG. 9 is perspective view of a modular embodiment of an exemplary air slide analyzer.

Air slides can be located in locations in a plant that may be difficult to access. Thus, in some instances, it is beneficial if the air slide analyzer can be assembled in locations where a crane or other lifting means is challenging or not feasible. FIG. 9 illustrates an embodiment 900 where an analyzer shielding 950 is designed with modular parts. For example, a block 901 is built out of material suitable for a PGNAA analyzer, such as polyethylene filled with shielding material, or other applicable material. Of course, other materials may be used, according to design preference. The design is modular such that each block 901 can be easily ported to the analyzer installation site, or alternately the analyzer shielding 950 can be moved as one unit. The block 901 may be configured with mating edges or protrusions to align/mate with adjacent blocks, or be "mated" via an adhesive or other coupling compound. The block(s) 901 can be substantially uniform in shape, enabling the air slide analyzer to be constructed or dismantled in a piece-wise manner. Use of modular assemblies that are light enough to be carried by hand provides flexibility in the installation location of the analyzer shielding 950.

Where physical space is not limited, the entire analyzer shielding 950 may be fabricated in a few large modules, or the small modular parts or larger modules can be externally assembled into one complete assembly. For example, for fitting over an existing air slide, the modules may be configured with individually assembled top, bottom, side sections that "fit" around the air slide to expedite assembly at the plant. Other combinations of "sizes" or geometries or stacking arrangement are understood to be within the purview of those skilled in the art. Therefore, alternative assembly or design methods can be used for the manufacture of an exemplary air slide analyzer. The assembly can also include additional shielding that is used in the front or back of the system that surrounds the air slide or part of the air slide. This allows for additional safety shielding for the system. This shielding can be attached, or in a separate attachment to the system.

Figure 10:
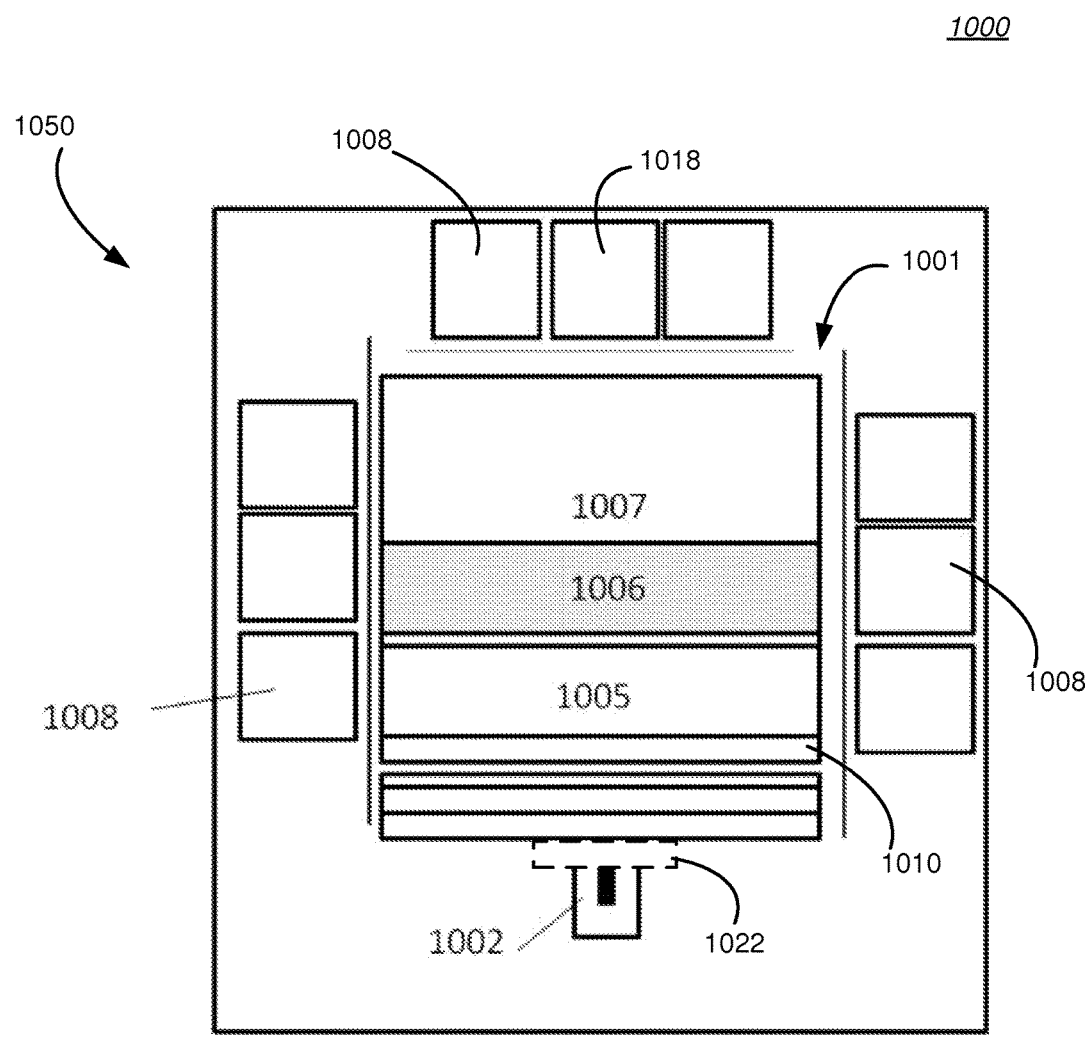
FIG. 10 is a cross-sectional view of an embodiment of an exemplary air slide analyzer with multiple detectors.

FIG. 10 illustrates a cross-sectional view 1000 of an embodiment of an exemplary air slide analyzer 1050 with air slide tunnel 1007 containing material in the "lower" region 1006 of the tunnel 1007. In this illustration, nine detectors 1008 are used, shown distributed outside the "sides" and "top" of the air slide 1001. The number of detectors 1008 used can vary from one to many detectors depending on different factors such as the size of the air flow chamber, the amount of material traveling through the analyzer 1050, the performance required, and other factors. Also, the shape of the air slide analyzer 1050, while illustrated as rectangular, may be any other desired geometrical shape. The neutron source 1002 is located at the bottom below the air chamber 1005 of air slide 1001, shown here with shielding and/or moderating material 1010. Other locations for the neutron source 1002 can be utilized according to design preference. For example, the neutron source 1002 can be located inside the air chamber 1005, or the source 1002 can be located at the side, and the detectors 1008 moved to different locations, on either side of the tunnel 1007, or even beside the neutron source 1002, separated by an adequate amount of neutron attenuating materials. The neutron source 1002 can be an isotopic source, a neutron generator 1022, or some combination involving one or both of these with some other source, if desired. In an exemplary embodiment, the system can have provisions for a neutron generator 1022 and an isotopic source 1002 that both can be used at the same time, or either one can be used.

Also, it is envisioned that another detector or sensor 1018 (illustrated as directly above the tunnel 1007) can be used in conjunction with the neutron based analysis, such as a Laser inducted breakdown spectroscopy (LIBS), Near infrared imaging (NIR), Nuclear Magnetic Resonance (NMR), X-ray Fluorescence, or X-ray diffraction. Of course, this other sensor 1018 may be located at another location in the analyzer 1050 or air slide 1001 or outside the analyzer, according to design preference.

In an alternate embodiment, the air chamber 1005 can be eliminated for a very short lengthwise span, and the neutron source 1002 (or generator 1022) may be located in this area. In another alternate embodiment, the neutron source 1002 (or generator 1022) could be located in the actual tunnel 1007. Yet in another embodiment, the neutron source 1002 (or generator 1022) could be located in the material 1006. Yet another embodiment can have the neutron source 1002 (or generator 1022) located in the top of the tunnel 1007 or above the air slide 1001. In short, many alternative configurations and arrangements are possible.

In various embodiments, the size and shape of the air chamber 1005 can be designed to optimize the signal from the material shown in region 1006 traveling through the analyzer 1050. For example, the width of the tunnel 1007 can be constricted to increase the depth of the material in region 1006 in its lower region (for example, as in a trapezoid or other narrowing geometry). Alternatively, the tunnel 1007 (and ensuing material occupying region 1006 in tunnel 1007) can be shaped to allow for overflow of the material in region 1006 to improve the signal or other aspects that may be desirable. This "shaping" of the tunnel 1007 (and lower region 1006) has been based on extensive modeling, with the resulting configuration designed to minimize the distance between the gamma ray emission from the material and the detectors and their respective configuration, while ensuring that gamma rays are captured from all regions containing the material. The design also minimizes the neutrons that impact the detector ensuring the best signal from the material in the analyzer 1050. Shielding material (not shown) for the detectors 1008 can be various different materials to shield the detectors 1008 from neutrons traveling into the detectors 1008, or to shield from lower energy gamma rays, or minimize background gamma rays, direct or indirect that would be otherwise absorbed and counted. To optimize the signal, the air chamber 1005 depth or size can be reduced or modified so that the neutron source 1002 is located closer to the material 1006. For example, the chamber 1005 can have a width optimized between 6" to 36", depending the particulars of the air slide 1001.

Figure 11:
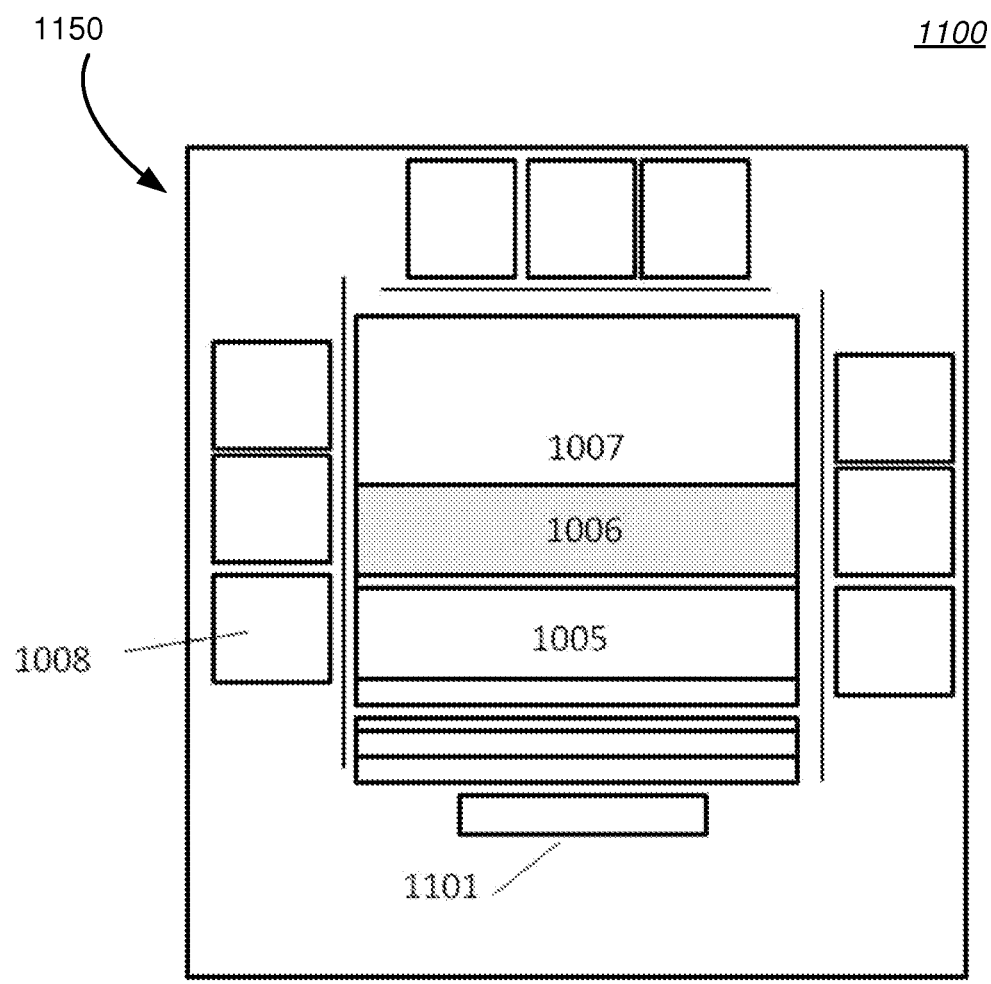
FIG. 11 is a cross-sectional view of an embodiment of an exemplary air slide analyzer including the source.

FIG. 11 is a cross-sectional view 1100 of an another embodiment using a neutron generator 1101 instead of a radioactive (e.g., californium) source. This can be a pulsed or continuous deuterium-deuterium generator, a Deuterium-Tritium generator, or a Tritium-Tritium generator, and so forth. The geometry and shape of the air slide analyzer 1150 can be modified to improve the performance of the analyzer depending on the type of material, the flow of material, the flow rate, the required system performance and other factors impacting the system performance, capabilities, and cost. As in FIG. 10, if both a neutron generator 1101 and an isotopic source (not shown) are used, then the isotopic source can be located proximate the neutron generator 1101. Thus, the system can either use an isotopic source, a neutron generator 1101, or both either separately or at the same time.

Figure 12:
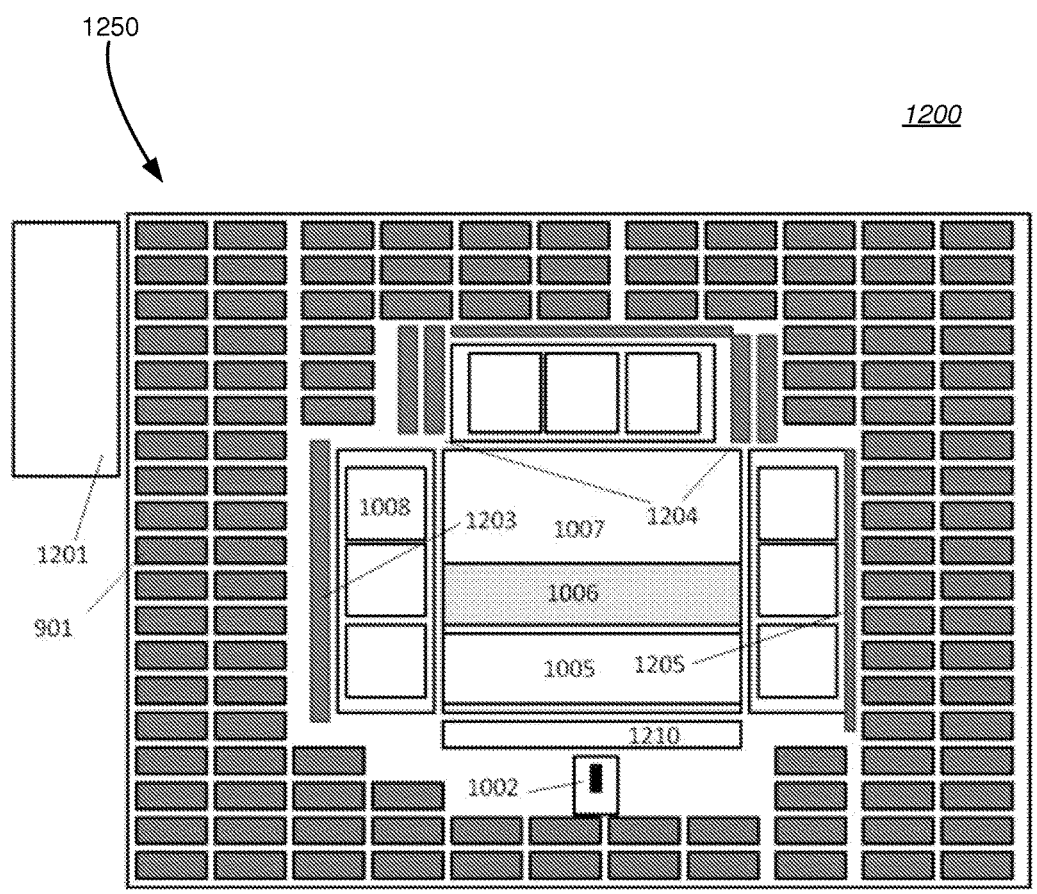
FIG. 12 is a cross-sectional view of an embodiment of an exemplary air slide analyzer configurable for various sizes of air slides.

FIG. 12 is a cross-sectional view 1200 of an air slide analyzer 1250 embodiment using smaller blocks 901 for shielding and construction. This design can handle different size of air slides. For example, the shielding material shown here at locations 1203, 1204, and 1205 can be made of polyethylene sheet, and its thickness can be varied to account for different air slide sizes. For a much wider air slide, the tunnel size 1007 (1006/1005) can be increased by using more (or re-arranging) blocks 901 and then filing the spacing the spacing between the blocks 901 and the air slide with shielding material (as shown, for example, at locations 1203, 1204, 1205) and other locations requiring shielding. The amount of emitted radiation can also be adjusted by varying the number of blocks 901 used either in the width of the system, the height of the system, or both. Alternately additional blocks 901 or shielding material can be used in front of or behind the analyzer 1250 to decrease the radiation in front of or behind the system. The shielding can be in blocks or other forms, and can either be attached to the system or separate. Also, shielding and/or moderating material 1210 can be placed proximal to the neutron source 1002, if so desired. This shielding/moderating material 1210 can operate to better "direct" the neutrons to the desired section of the air slide.

The analyzer control box 1201 can house the detector electronics, the power supply, the analyzer computer and other parts of the system. In the simplest embodiments, the electronics and power supplies for the system are located in this control box 1201, and the analysis computer is located in a remote location, or alternately located inside the control box 1201. Of course, many other different configurations and geometries are possible.

Figure 13:
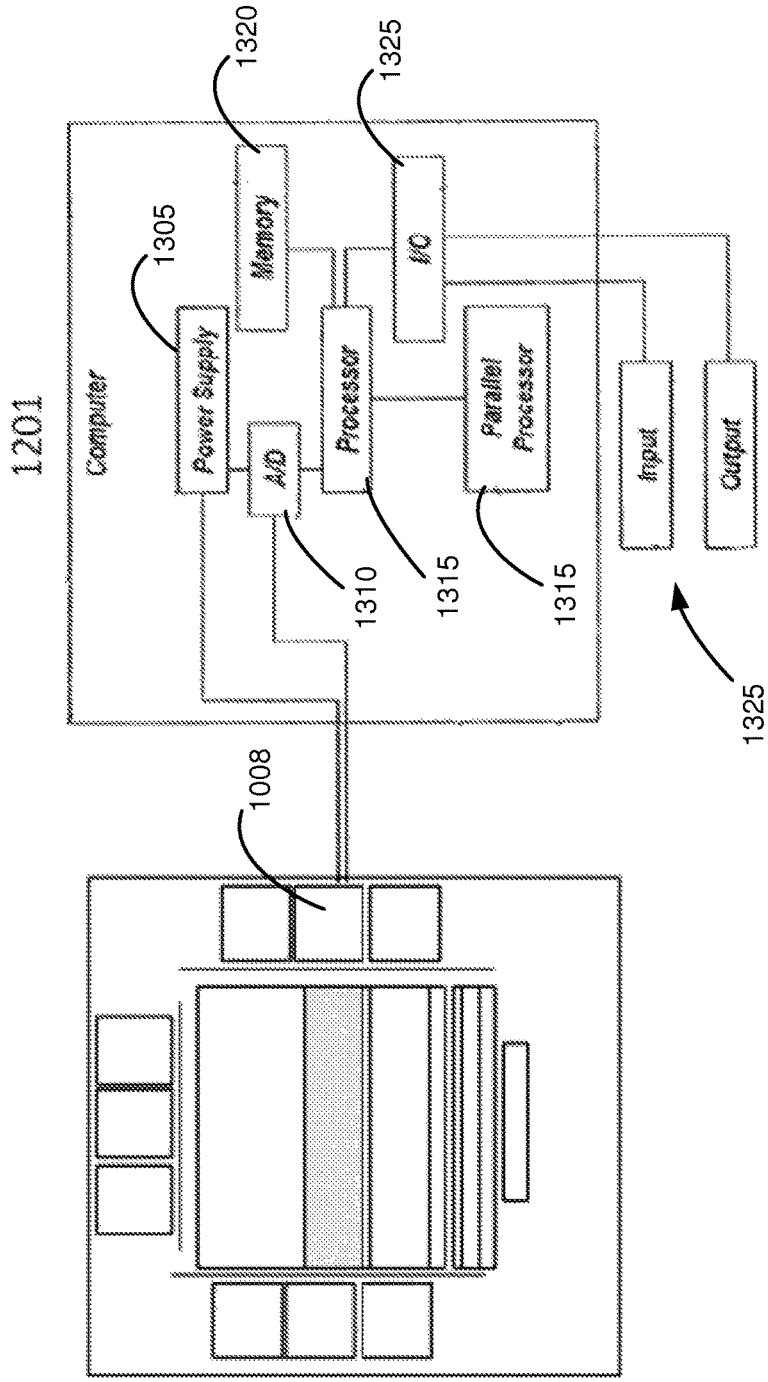
FIG. 13 is a component illustration of control hardware.

FIG. 13 is an illustration 1300 of one possible embodiment for the control box 1201 components. Control box 1201 can contain power 1305 for the detectors 1008, an analog to digital converter 1310 to capture the data from the detector 1008, one or more processors 1315 with memory 1320 to handle and analyze the data, and to store the data. The interface 1325 to the system can be provided on a dedicated computer, or alternatively provided through a web-based interface. Neutron-based analyzers have been in existence for over 25 years, and alternative control box 1201 implementation paradigms are within the scope of one of ordinary skill in the art.

Figure 14:
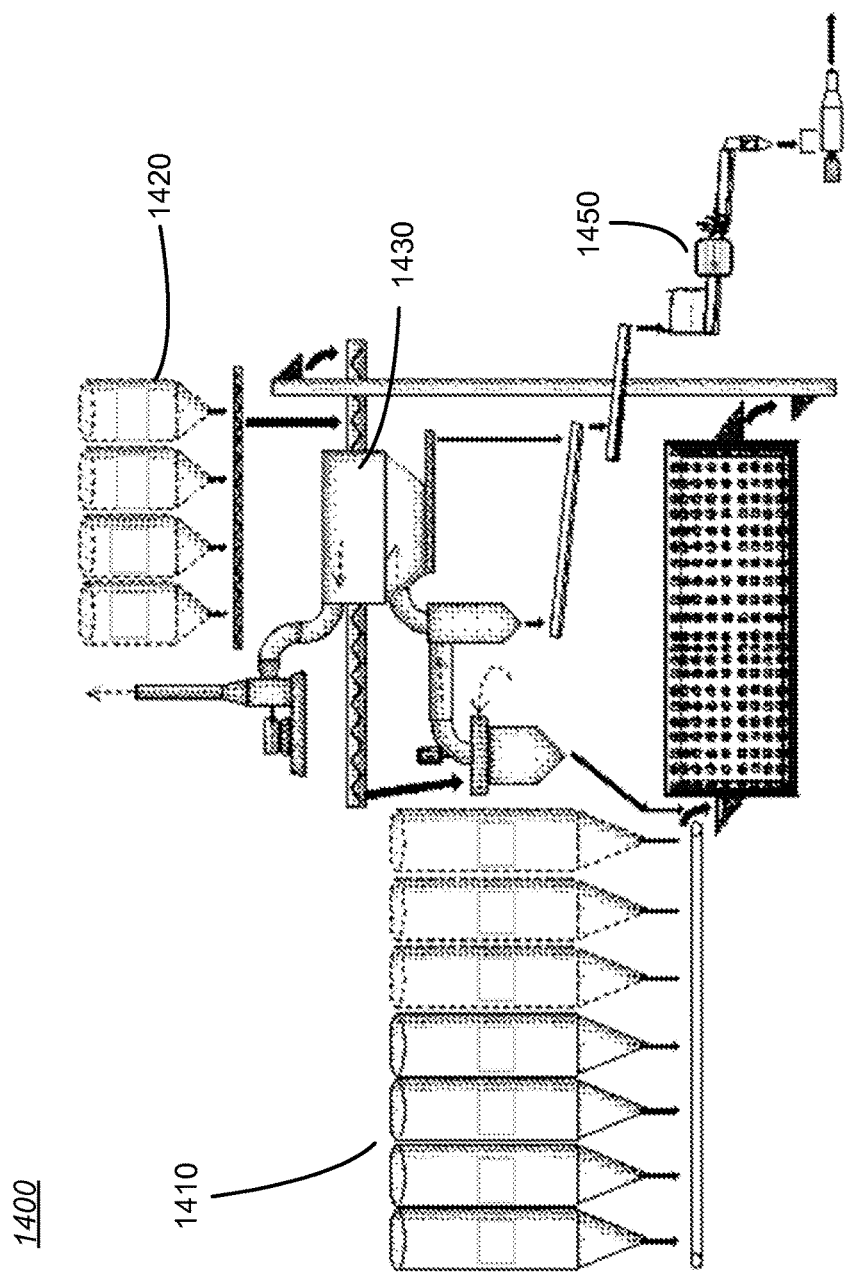
FIG. 14 is a schematic illustration of an exemplary slide analyzer in a cement manufacturing environment.

FIG. 14 is an illustration 1400 of an exemplary air slide analyzer 1450 in a commercial cement industry setting. Multiple different silos 1410, 1420 contain material such as clinker, off-spec clinker, gypsum, limestone, lime, marble, granite, shale, sand, sandstone, gravel, mill scales, iron ore, bauxite, volcanic ores, bottom ash, beneficiated fly ash, slag, and so forth. Of course, depending on the type of "cement" being created, other materials may be contemplated. This material is run through a ball mill 1430 and then analyzed by the air slide analyzer 1450. The measurement information from the air slide analyzer 1450 is used to dynamically adjust, via feedback controls (not shown), the mixture of material that is being blended together. Using this method, it is possible to dynamically adjust the material to have the required composition that is optimal or very close to optimal for the cement plant operations, and provides very consistent product for the end-customers. There are many other possible locations where an exemplary air slide analyzer 1450 can be used, so any of these locations can be used for the analysis. The exact location and use may vary depending on plant operations and needs of the site.

Another potential application is the analysis of hot meal after pre-heating or calcining (conversion of carbonated minerals to mineral oxides), just before the hot meal enters the kiln. This can be used to monitor, control or adjust the materials added after the milling, such as fly ash and other materials. The material analysis data the system provides can also be utilized in synergy with other analytical instrumentation (including PGNAA systems) in the plant, other process control software and systems, to dynamically control the manufacturing process. The system can also be used to blend raw mix, as well as additives that are added before and after the milling process in finished cement production. Yet another potential application is with the analysis of blending of finished cement with aggregate material at ready-mix sites.

While the embodiment of FIG. 14 is in the context of a commercial cement industry setting, it is expressly understood that the exemplary air slide analyzer in the above figures. may also be utilized in other industries that require analysis of aggregated materials. Non-limiting examples may be the food, chemical, pharmaceutical industries, and so forth.

Furthermore, while repeated references are made to PGNAA as the method of choice, other applicable methods/systems may be implemented. For example, where neutrons enter the material to be analyzed, and gamma rays emitted, gamma spectroscopy can be performed on the resulting spectra to extract the measurement information. Therefore, the "analysis" mechanism is not limited to PGNAA, but can include neutron activation analysis that use fast neutrons, thermal neutrons or all types of neutrons, which is often referred to in general as neutron activation analysis. Thus, the various embodiments described herein can encompass PGNAA, as well as analysis using such industrially used acronyms such as PFNA, PFTNA, PTNA, and other terms common to those familiar with this technology. Accordingly, in some embodiments multiple analysis mechanisms can be implemented, a first analyzer in a "forward" part of the air slide and a second (or more) analyzer in the "rear" part of the air slide (perhaps performing a different kind of analysis, such as analysis for heavy element contaminants). Consequently, various combinations of sources, detectors, analysis schemes, etc. can be implemented, according to design preference.

Yet another implementation is to use another sensor in conjunction with the neutron based analysis, such as a Laser inducted breakdown spectroscopy (LIBS), Near infrared imaging (NIR), or other techniques, and to use this neutron-based measurement to correct or adjust the other sensor, or alternately use the other sensor to adjust the neutron measurements. This can be incorporated inside the analyzer or in two or more separate units. Additional measurement can also be taken and combined with the system. For example, samples may be extracted at the weir gate or other location, and molecular analysis can be done. Thus, the system could then provide both elemental and molecular analysis.

It should be understood that various elements/features/components of the described embodiments may be reconfigured, altered, modified, according to design preference. For example, the air slide analyzer can be on slight angle, horizontal, or at any angle. The detector can be located separately from the analyzer body, the source can be separate from the analyzer body, and the shielding can be separate from the analyzer body. If the detector, shielding and neutron source are separate parts, there may be no clear body to the analyzer. The air slide does not have to have air from below, but the material may be blown or conveyed through the analyzer by other means such as by using a steeply inclined surface. To those skilled in the art, the analyzer shape and size and configuration can vary. What is consistent is that the material travels to or from the analyzer by an air slide, and the material composition is measured by the analyzer.

It should be further understood that this and other arrangements described herein are for purposes of example only. As such, those skilled in the art will appreciate that other arrangements and other elements (e.g. machines, interfaces, functions, orders, and groupings of functions, etc.) can be used instead, and some elements may be omitted altogether according to the desired results. Further, many of the elements that are described are functional entities that may be implemented as discrete or distributed components or in conjunction with other components, in any suitable combination and location. For example, the functional blocks, methods, devices and systems described in the present disclosure may be integrated or divided into different combinations of systems, devices, and functional blocks, as would be known to those skilled in the art.

Many modifications and variations can be made without departing from its scope, as will be apparent to those skilled in the art. Functionally equivalent methods and apparatuses within the scope of the disclosure, in addition to those enumerated herein, will be apparent to those skilled in the art from the foregoing descriptions. It is to be understood that this disclosure is not limited to particular methods, implementations, and realizations, which can, of course, vary. It is also to be understood that the terminology used herein is for the purpose of describing particular embodiments only, and is not intended to be limiting. The various aspects and embodiments disclosed herein are for purposes of illustration and are not intended to be limiting, with the true scope being indicated by the following claims.

The invention claimed is:

1. An air slide analyzer for measuring the elemental content of aerated material traveling by air slide, the air slide analyzer comprising:

an analyzer having an entrance opening and an exit opening, and an interior tunnel adapted for aerated material conveyed by an air slide;
an air slide adjacent to the tunnel;
a radiation detector proximal to the analyzer;
a source of neutrons emitting neutrons into material within the analyzer;
a processor to analyze detected information from the radiation detector, wherein emissions from the material being irradiated with neutrons are detected by the radiation detector and analyzed by the processor to provide elemental information of the material in the analyzer; and
a mechanism for increasing a mass per length of material of the material above a mass level per length flowing in a standard air slide section without an analyzer.

2. The air slide analyzer of claim 1, wherein the analysis is at least one of prompt gamma neutron activation analysis (PGNAA), Thermal Neutron Analysis (TNA), Pulsed Fast Neutron Analysis (PFNA), Pulsed Thermal Neutron Analysis (PTNA), Pulsed Fast Thermal Neutron Analysis (PFTNA) and Fast Neutron Analysis (FNA).

3. The air slide analyzer of claim 1, further comprising a complimentary measurement system using at least one of Laser induced breakdown spectroscopy (LIBS), Near infrared imaging (NIR), spectral imaging, X-ray diffraction, X-ray fluorescence, and Nuclear Magnetic Resonance.

4. The air slide analyzer of claim 1, wherein the source of neutrons is at least one of a radioisotope neutron source and a controllable neutron generator.

5. The air slide analyzer of claim 1, wherein a portion of the air slide is within the air slide analyzer and the portion is comprised of a material that absorbs fewer neutrons than steel or aluminum.

6. The air slide analyzer of claim 1, wherein the mechanism is at least one movable gate disposed within the air slide.

7. The air slide analyzer of claim 1, further comprising a mixer in the tunnel, the mixer mixing material in the tunnel for homogenization, either before or within in a material accumulation area of the tunnel.

8. The air slide analyzer of claim 1, further comprising at least one of a heater and cooler to heat or cool the detector or control the detector temperature.

9. The air slide analyzer of claim 1, further comprising an active cooling channel between the air slide and the detector.

10. The air slide analyzer of claim 1, further comprising a neutron moderator to optimize signal from the air slide analyzer.

11. The air slide analyzer of claim 1, further comprising a least one of gamma ray absorber or neutron absorber disposed about the analyzer, to minimize direct and/or indirect background radiation that would contribute to an external biological radiation dose emanating from the air slide analyzer.

12. The air slide analyzer of claim 1, further comprising shielding located at least one of a front, side, top, bottom and back area arranged to reduce external radiation for biological shielding.

13. The air slide analyzer of claim 12, wherein the analyzer is comprised of a plurality of substantially uniformly shaped, individual, shielding pieces, enabling the analyzer to be constructed or dismantled in a piece-wise manner.

14. The air slide analyzer of claim 1, further comprising an opening within the air slide for at least one of physically sampling material directly from the air slide and placing a calibration standard in the air slide.

15. The air slide analyzer of claim 1, wherein the air slide is comprised of multiple sections, wherein the air slide section(s) can be replaced for maintenance or for calibration by a standard section(s) of an air slide.

16. The air slide analyzer of claim 1, wherein the accumulation area of the air slide in the body is designed with a shape and size that improves a signal accuracy of the air slide analyzer.

17. The air slide analyzer of claim 1, further comprising material in the air slide, the material being at least one of, raw meal, finished cement, a blend of finished cement and aggregates, ready-mix concrete, fly ash, gypsum, limestone, clinker, off-spec clinker, bottom ash, slag, beneficiated fly ash, lime, silica fume, ground granulated blast furnace slag, shale, sand, sandstone, iron more, bauxite, volcanic ore, and ash.

18. The air slide analyzer of claim 17, further comprising silos containing at least one of the materials.

19. The air slide analyzer of claim 18, wherein the processor sends information for adjusting an amount of material supplied from the silos based on the at least one molecular and elemental composition of the material in the air slide.

20. The air slide analyzer of claim 1, wherein the material measurement is used with measurement information from one or more cross belt prompt gamma neutron activation analysis (PGNAA) systems.

* * * * *